United States Patent [19]

Jung et al.

[11] Patent Number: 5,338,876

[45] Date of Patent: Aug. 16, 1994

[54] ALKENYCHLOROSILANES AND DIRECT SYNTHESIS THEREOF

[75] Inventors: Il N. Jung, Seoul; Seung H. Yeon, Kyungki-Do; Bong W. Lee, Kwangju; Bok R. Yoo, Seoul, all of Rep. of Korea

[73] Assignee: Korea Institute of Science and Technology (KIST), Seoul, Rep. of Korea

[21] Appl. No.: 75,134

[22] Filed: Jun. 10, 1993

[30] Foreign Application Priority Data

Jun. 13, 1992 [KR] Rep. of Korea ............. 10292/1992

[51] Int. Cl.$^5$ .................... C07F 7/08; C07F 7/16
[52] U.S. Cl. .................... 556/431; 556/465; 556/472; 556/487
[58] Field of Search ............. 556/431, 472, 487, 465

[56] References Cited

U.S. PATENT DOCUMENTS

| | | | |
|---|---|---|---|
| Re. 33,452 | 11/1990 | Ward, III et al. ............. | 556/472 |
| 2,380,995 | 8/1945 | Rochow ............. | 260/607 |
| 2,420,912 | 5/1947 | Hurd ............. | 556/472 |
| 2,642,447 | 6/1953 | Plueddemann ............. | 556/465 |
| 3,536,743 | 10/1970 | Schrader et al. ............. | 556/472 |
| 3,560,545 | 2/1971 | Schrader et al. ............. | 556/472 |
| 4,268,682 | 5/1981 | Oswald et al. ............. | 556/465 |
| 4,661,613 | 4/1987 | Prud'Homme et al. ............. | 556/472 |
| 4,973,725 | 11/1990 | Lewis et al. ............. | 556/472 |
| 5,015,751 | 5/1991 | Feldner et al. ............. | 556/472 |
| 5,075,477 | 12/1991 | Jung et al. ............. | 556/435 |
| 5,206,402 | 4/1993 | McVannel et al. ............. | 556/465 |
| 5,233,069 | 8/1993 | Jung et al. ............. | 556/435 |
| 5,250,716 | 10/1993 | Mui ............. | 556/472 |

OTHER PUBLICATIONS

V. V. Korshak, A. M. Polyakova, V. F. Mironov, A. D. Petrov, and Tambovtseva, Izvst. Akad. Nauk S.S.S.R., Otdel. Khim. Nauk., 1116 (1959).

Bazant et al., *Organosilicon Compounds*, vol. 2, Part 1, Academic Press, (N.Y.), 1965, pp. 63 and 88.

D. T. Hurd and G. F. Roedel, *Vinyl and Allyl Silicone Polymers and Copolymers*, Ind. Eng. Chem., 40, 2079 (1948).

E. G. Rochow, *Organosilicon Halides*, (Aug. 7, 1945); C.A. 39, 4889 (1945).

E. G. Rochow, *The Direct Synthesis of Organosilicon Compounds*, J. Am. Chem. Soc., 67, 963 (1945).

P. Trambouze and D. Imelik, *Catalysts Bases on Copper Used in the Synthesis of Methylchlorosilanes*, J. Chim. Phys., 51, 505 (1954); C.A. 49, 14635c (1955).

(List continued on next page.)

*Primary Examiner*—Paul F. Shaver
*Attorney, Agent, or Firm*—Darby & Darby

[57] ABSTRACT

Alkenylchlorosilane of formula I and a direct synthesis thereof are disclosed, wherein silicon metal is reacted with mixed gas comprising alkenyl chloride of formula II and hydrogen chloride or alkyl chloride of formula III in the presence of copper catalyst at a temperature range from 220° C. to 350° C.

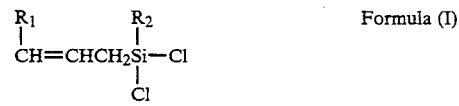

Formula (I)

In formula I, $R_1$ represents hydrogen, methyl, $SiHCl_2$, $SiCl_3$ or $CH_2SiCl_3$ and $R_2$ represents hydrogen or chlorine.

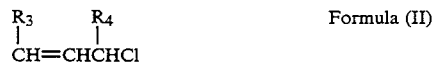

Formula (II)

In formula II, $R_3$ represents hydrogen or chlorine and $R_2$ represents hydrogen, methyl or $CH_2Cl$.

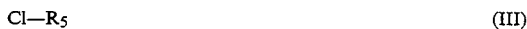

$Cl-R_5$ (III)

In formula III, $R_5$ represents hydrogen, $C_1$-$C_4$ alkyl or $CH_2CH_2Cl$.

19 Claims, No Drawings

OTHER PUBLICATIONS

E. G. Rochow, *In Inorganic Synthesis*, III, McGraw-Hill, New York, 1950, p. 5b.

A. L. Klebanski and V. S. Fikhtengol'ts, *Synthesis of Organosilicon Compounds, III. The Reaction of Direct Synthesis of Methylchlorosilanes, J. Gen. Chem.* S.S.S.R., 27, 2693 (1957); C.A. 52, 7131d (1958).

J. C. Vlugter and R. J. H. Voorhoeve, Conf. Accad, Lincei: Alta. Tech. Chim, 1961, p. 81 (1962)–from the text reference; R. J. H. Voorhoeve.

H. Grohm and R. Paudert, *Reaction of Silicon with Carbon Tetrachloride while milling, Chem. Tech.*, 10, 307 (1958).

J. M. Dotson, French Patent 1,311,472; reference from an article–J. M. Dotson, *Extending the Range of Jet Mills, Ind. Eng. Chem.* 54(2), 62 (1962).

J. E. Sellers and J. L. Davis, *Organosilicon Compounds,* U.S. Pat. No. 2,449,821 (Sep. 21, 1948); C.A. 43, 1051b (1949).

B. A. Bluestein, *Alkylhalosilanes,* U.S. Pat. No. 2,887,502 (May 19, 1959); C.A. 53, 18865c (1959).

R. J. H. Voorhoeve, *Organohalosilanes–Precursors to Silicones,* Elsevier Publishing Company, New York, 1967.

D. T. Hurd, *The Preparation of Vinyl and Allyl chlorosilanes, J. Am. Chem. Soc.,* 67, 1813 (1945).

V. F. Mironov and A. D. Petrov, *Synthesis and Polymerization of Compounds Containing Hydrogen at the Silicon Atom and an Unsaturated Radical,* Izvest. Akad. Nauk S.S.S.R., Otdel, Khim. Nauk 383 (1957).

A. D. Petrov, S. I. Sadykh–Zade, E. A. Cheryshev, and V. F. Mironov, *Direct Synthesis of Alkylpolysilane Chlorides, Zh. Obshch. Khim.*, 26, 1248 (1956) 17, p. 6, line 9.

A. D. Petrov, S. I. Sadykh–Zade, N. P. Smetankina, and Yu. P. Erorov, *Direct Synthesis of Chlorosilanes from Vinyl and Allyl Dichlorides, Zh. Obshch. Khim.,* 26, 1255 (1956).

A. D. Petrov, G. I. Nikishim, N. P. Smetankina and Yu. P. Erorov, *Synthesis of 1,1–Dichlorocyclosilico–3–pentene,* Izvest. Akad., Nauk S.S.S.R.. Otdel. Khim. Nauk 947, (1955).

ALKENYCHLOROSILANES AND DIRECT SYNTHESIS THEREOF

FIELD OF THE INVENTION

The present invention relates to alkenylchlorosilanes of formula I and a process for preparing the same as the major products by directly reacting silicon metal simultaneously with alkenyl chloride of formula II and hydrogen chloride or alkylchlorides of formula III in the presence of copper catalyst at a temperature from 220° C. to 350° C. The preferred reaction temperature range is 300°-330° C. Useful copper catalysts include copper metal, copper salts, and partially oxidized copper.

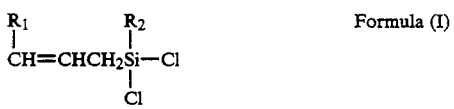

Formula (I)

In formula I, $R_1$ represents hydrogen, methyl, $SiHCl_2$, $SiCl_3$, or $CH_2SiCl_3$ and $R_2$ represents hydrogen or chlorine.

Formula (II)

In formula II, $R_3$ represents hydrogen or chlorine and $R_4$ represents hydrogen, methyl or $CH_2Cl$.

(III)

In formula III, $R_5$ represents hydrogen, $C_1$-$C_4$ alkyl or $CH_2CH_2Cl$. Alkenylchlorosilanes having two functional groups of alkenyl group and Sl—H group will be useful for the manufacture of silicones, because they can undergo various reaction such as hydrosilylation, Friedel-Crafts reaction, etc. (V. V. Korshak, A. M. Polvakova, V. M. Mironov, A. D. Petrov, and Tambovtseva, Izvst. Akad. Nauk S.S.S.R., Otdel, Khim, Nauk, 1116 (1959), D. T. Hurd and G. F. Roedel, Ind. Eng. Chem., 40, 2079 (1948)).

DESCRIPTION OF THE PRIOR ART

Methylchlorosilanes are the most important starting materials for silicones. E. G. Rochow discovered the direct process for the synthesis of methylchlorosilanes, reacting elemental silicon with methyl chloride in the presence of a copper catalyst in 1940 (E. G. Rochow, U.S. Pat. No. 2,380,995),

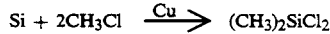

The reaction gives not only dimethyldichlorosilane, but also methyltrichlorosilane, trimethylchlorosilane and tetrachlorosilane. A number of high boiling compounds are also found in the mixture of the products in a small quantity. The reaction rate and the nature of products depend on a large number of factors. These determining factors include the nature of the starting materials, the catalyst, the reaction temperature, the reaction pressure, the type of reactor used, and the degree of conversion of silicon and methyl chloride.

The catalyst for the direct process is always copper, and in some cases co-catalysts such as zinc, aluminum, cadmium etc. are added. The co-catalysts enhance the reactivity of silicon metal and shorten the induction period and increase the selectivity of dimethyldichlorosilane production. The reaction is carried out at 250°-350° C., and the yield of dimethyldichlorosilane decreases at temperatures above 300° C. In the absence of a catalyst, the reaction is sluggish and gives irreproducible results (E. G. Rochow, J. Am. Chem. Soc., 67, 963 (1945)). The composition of the products depends on the amount of copper used. The greater amount of copper is used, the higher is the chlorine content of the resulting products. The greatest catalytic efficiency is obtained when the amount of copper is 10% of the amount of Silicon, The reactivity of the silicon-copper mixture is connected with the formation of an intermetallic $\eta$-phase ($Cu_3Si$). The presence of the $\eta$-phase in the mixture Is of fundamental importance for the selective synthesis of dimethyldichlorosilane. It is known that the mixture of silicon powder and copper powder is heated 800° to 1,000° in nitrogen, or better in hydrogen, the powders become sintered and the $\eta$-phase is formed (P. Trambouze and B. Imelik, J. Chim, Phys., 51, 505 (1954)). The $\eta$-phase is also chemically prepared by heating cuprous chloride with silicon at the temperature above 350° C. (E. G. Rochow in Inorganic synthesis, III. McGraw-Hill, New York 1950, p56).

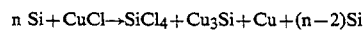

The reaction rate and the composition of the products in the direct synthesis are highly temperature-dependent (A. L. Klebamskii and V. S. Fikhtengolts, J. Gen. Chem. U.S.S.R., 27, 2693 (1957)). It is much important to maintain the reaction temperature at an accurately specified temperature and to prevent any hot spot developing in the agglomerates of the solid phase. It is reported that at higher temperatures, the deposition of carbon on the surface of the metal mixture occur which slows down the reaction (J. C. Vlugter, and R. J. H. Voorhoeve, Conf. Accad. Lin-cei, Alta Tech. Chim. 1961 p81 (1962)). This is why the reactor for the direct synthesis of methylchlorosilane must have a high thermal stability and an efficient heat transfer.

The direct process can be carded out in fixed bed, in stirred bed, and also in fluidized bed reactors. The process with the stirred bed reactors has the advantages over the fixed bed operation that the heat of reaction can be removed more easily and the movement of the powders causes fresh surface to be continuously exposed (H. Grohm and R. Paudert, Chem. Techn. 10,307 (1958)). Sellers and Davis reported that a mechanically stirred fluidized bed could be used (J. E. Sellers and J. L. Davis, U.S. Pat. No. 2,449,821). The metal powder was agitated in an up and down motion in a vertical reactor by means of spiral band rotated by a central shaft while a stream of methyl chloride was upward through it. Bluestrim used a fluidized bed reactor for the production of methylchlorosilane (B. A. Bluestrim, U.S. Pat. No. 2,887,502). Dotson further improved the fluidized-bed process by continuously or intermittently removing a portion of the solid powder from the reactor space and grinding it in a jet mill before returning it to the reactor (J. M. Dotson, French Pat. 1,311,472).

Since the direct synthesis of methylchlorosilane from metallic silicon and methyl chloride, direct reactions of metallic silicon with various alkyl chloride have been studied extensively and reviewed in detail. The reactivity of alkyl chlorides and the type of major product are different depending upon the alkyl group (R. J. H. Voorhoeve, "Organohalosilanes-Precursors to Silicones", Elsevier Publishing Company, New York, 1967). Direct synthesis of allyldichlorosilane was first reported by Hurd in 1945 (D. T. Hurd. J. Am. Chem. Soc. 67, 1813 (1945)). When allyl chloride was reacted with a 9:1 Si—Cu alloy, a vigorous exothermic reaction occurred even at 250° C. The condensate obtained contained trichlorosilane, tetrachlorosilane, allyldichlorosilane, diallyldichlorosilane, and allyltrichlorosilane predominating due to the decomposition of allyl chloride during the reaction. However, this reaction has never been used on a large scale in industry, because of the decomposition of allyl chloride and the easy polymerization of diallyldichlorosilane at high temperature above 130° C.

Mironov and Zelinskii reported later that they obtained only 644 g of a mixture of allylchlorosilanes from the reaction of a 5:1 Si—Cu alloy with 2 kg of allyl chloride at 300° C. The product mixture contained 356 g of allyldichlorosilane, 185 g of allyltrichlorosilane, and 103 g of diallyldichlorosilane (V. M. Mironov and D. N. Zelinskii, Isvest. Akad. Nauk S.S.S.R., Otdel, Khim. Nauk 383 (1957)). The production of allyldichlorosilane and allyltrichlorosilane indicates that allyl chloride decomposed under the reaction conditions and dehydrochlorination or dechlorination were accompanied. This is why the yield was under 30%, indicating that the process was economically feasible.

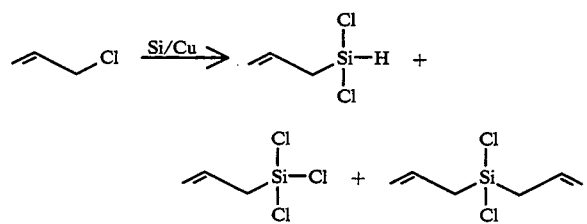

Petrov and his co-workers reported that they obtained a small amount of allyltrichlorosilane and propenyltrichlorosilane by reacting silicon metal with 1,3-dichloro-1-propene in the presence of a copper catalyst at the reaction temperature of 370° C.–380° C. (A. D, Petrov, S. I. Sadyth-Jade, E. A. Cheryshev, and V. F, Mironov, Zh. Obshch, Khim., 26, 1248 (1956), A. D. Petrov, S. I. Sadyth-Jade, N. P. Smetankina, and Yu. P. Egorov, Zh. Obshch, Khim., 26, 1255 (1956)). They also reported the same reaction using 3,4-dichloro-1-butene instead of 1,3-dichloro-1-propene. They obtained 15.6% of 1,1-dichloro-1-silacyclopent-3-ene and 9% of 1,1,1,6,6,6-hexachloro-1,6-disilahexa-3-ene (A. D. Petrov, S. I. Sadyth-Jade, N. P. Smetankina, and Yu. P. Egorov, Isvest. Akad Nauk S.S.S.R., Otdel. Khim Nauk 947 (1955)). However, the reaction of silicon metal with a mixture of alkenyl chloride and hydrogen chloride has never been reported before.

We reported that the trisilaalkanes of formula V as the major products and bis(silyl)methanes of formula VI as the minor products were prepared by reacting α-chloromethylsilanes represented in formula IV with elemental silicon in the presence of copper catalyst at a temperature from 250° C. to 350° C. The copper catalyst was used 1–20% of total contact mixture, but the preferred amount was 5–10%. The reaction could be carried out in a fluidized bed or in a stirred bed reactor. Addition of micro-spherical acid clay to silicon metal improved the fluidization and gave better results (I. N. Jung, G. H. Lee., S. H. Yeon, M. Suk, U.S. Pat. No. 5,075,477 (Dec. 24, 1991)).

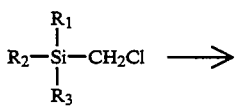

Formula IV

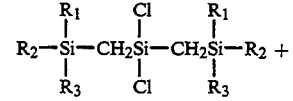

Formula V

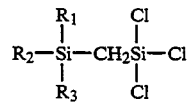

Formula VI wherein $R_1$, $R_2$, and $R_3$ may independently be chlorine or methyl.

We also reported that the direct synthesis of Si—H containing bis(silyl)methanes by reacting silicon metal with a mixture of α-chloro-methylsilanes and hydrogen chloride. The bis(silyl)methane containing dichlorosilyl group was obtained as the major product and bis(-silyl)methane containing trichlorosilyl group was obtained as the minor product. The major product could be explained by the reaction of the same silicon atom with each mole of two starting materials. The results suggest that the reactivities of the two starting materials were not much different. The major portion of the other by-products was trichlorosilane and tetrachlorosilane which were produced from the reaction between silicon metal and hydrogen chloride (Korean Patent Application No. 91-24243).

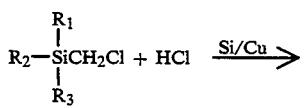

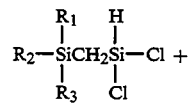

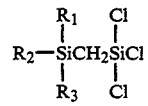

wherein $R_1$, $R_2$, and $R_3$ may independently be chlorine or methyl.

SUMMARY OF THE INVENTION

It is an object of the present invention to provide alkenylchlorosilane of formula I.

It is another object to provide a method for preparing alkenylchlorosilanes by directly reacting silicon metal simultaneously with alkenyl chloride of formula II and hydrogen chloride or alkyl chlorides of formula III to give alkenyldichlorosilanes of formula I as the major products in the presence of copper catalyst at a temperature from 220° C. to 350° C. The preferred reaction temperature range is 300°–330° C. Useful copper catalysts include copper metal, copper salts, and partially oxidized copper.

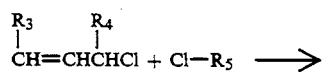

Formula II    Formula III

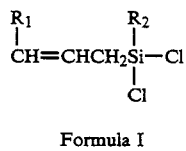

Formula I

In formula I, $R_1$ represents hydrogen, methyl, $SiHCl_2$, $SiCl_3$, or $CH_2SiCl_3$ and $R_2$ represents hydrogen or chlorine. In formula II, $R_3$ represents hydrogen or chlorine and $R_4$ represents hydrogen, methyl or $CH_2Cl$. In formula III, $R_5$ represents hydrogen, $C_1$–$C_4$ alkyl or $CH_2CH_2Cl$.

Other and further object, features and advantages of the invention will appear more fully from the following descriptions.

DETAILED DESCRIPTION OF THE INVENTION

The compounds of formula III may be illustrated as hydrogen chloride, 1,2-dichloroethane, propyl chloride, n-butyl chloride, or t-butyl chloride. When 1,2-dichloroethane was used, alkenyltrichlorosilane was the major product. The reactants of formulae II and III are blended before they are introduced to the reactor. They can be mixed in gaseous state after they are vaporized, or also in liquid state when formula III compound is a liquid. The blending ratio of the compound II to each mole of the compound III can be from 0.1 to 4.0 moles, but the preferred ratio is 1.0–2.0 moles. Since diallyldichlorosilane is not produced, the process is easier to run compared with the process without hydrogen chloride mixing.

The reaction can be carded out in a fluid bed or in a stirred bed reactor. In the fluidized bed reaction, the addition of inert nitrogen gas to the starting gases is recommended to improve the fluidization. This also helps to remove the high boiling products out of the reactor. The pressure at which the reaction of present invention is conducted is not critical and may be varied from 1 to 5 atmospheres, preferably 1 to 3 atmospheres. Metallurgical grade silicon was employed in the process of this invention, which contained higher than 95% silicon by weight. The preferred purity of silicon was higher than 98%. The particle size of the silicon was 1–200 micron, but 20–200 micron was used for the fluidized reaction. The reaction temperature was from 250° C. to 350° C. The preferred reaction temperature range was 280°–320° C. The reaction pressure was from 1 to 5 atmospheres. Addition of micro-spherical acid clay to silicon metal improved the fluidization and gave better results.

The commercially available copper catalysts for the reaction between silicon and methyl chloride are also found to be good catalysts for these reactions. The content of copper catalyst is 1–20% of total contact mass. The preferred copper content is 5–10%. The process in this invention is characterized to include promotors. The range of the promotors content is 0.001–5.0%. The promotors include calcium, barium, zinc, tin, cadmium, manganese, magnesium, silver, and chromium, but are not limited to them.

The invention will be further illustrated by the following examples. It is, however, not intended that this invention will be limited by the examples.

EXAMPLE 1

Preparation of Si/Cu contact mixture (I)

After about 360 g (325–60 mesh) of silicon is mixed with 62.3 g of CuCl (10% of copper based on the weight of the silicon and copper) as a catalyst in order to provide a mixture, the mixture is contained in the reactor. Thereafter, the mixture was heated to a temperature ranging from 180° C. to 250° C. At this time, the agitator rotates at 60 rpm. In order to mix the mixture completely together with blowing slowly dried nitrogen. When the temperature in the reactor is raised to about 370° C., the silicon reacts with the CuCl to form $\eta$-phase $Cu_3Si$, and $SiCl_4$ is obtained as a by-product which is removed from the reactor. In the case of using a promotor, 0.8 g of a promotor metal is added to the mixture after the reaction is completed.

EXAMPLE 2

Preparation of Si/Cu contact mixture (II)

In case of using metallic copper or copper catalysts which were used in the synthesis of methylchlorosilanes instead of the CuCl as described in EXAMPLE 1, 10% of the copper based on the weight of the silicon and copper was mixed with the silicon. The mixture was heated at 350° C. for 2 hours in the reactor together with blowing hydrogen chloride or methyl chloride in order to be activated.

The compositions of the contact mixtures prepared in Example 1 and 2 are shown in Table 1.

TABLE 1

| Sample No. | Si (g) | CuCatalyst Form | (g) | Promotor Metal | (g) | Metal | (g) | Remark |
|---|---|---|---|---|---|---|---|---|
| I-1 | 360 | CuCl | 62.3 | | | | | |
| I-2 | 380 | Cu | 20.0 | | | | | |
| I-3 | 360 | Cu | 40.0 | Cd | 2.0 | | | |
| I-4 | 360 | Cu | 40.0 | Zn | 2.0 | | | |
| I-5 | 380 | Cu | 20.0 | Cd | 2.0 | Sn | 0.02 | |
| I-6 | 380 | Cu | 20.0 | Ca | 2.0 | | | |
| I-7 | 380 | Cu | 20.0 | Ca | 2.0 | Cd | 2.0 | |
| I-8 | 360 | Cu | 40.0 | Ag | 2.0 | | | |
| I-9 | 360 | Cu | 40.0 | Ag | 2.0 | Cd | 2.0 | |
| I-10 | 360 | Cu | 40.0 | Mn | 2.0 | | | |
| I-11 | 360 | Cu | 40.0 | Mn | 2.0 | Cd | 2.0 | Acid clay added |
| I-12 | 360 | Cu | 40.0 | Mg | 2.0 | | | |
| I-13 | 360 | Cu | 40.0 | Mg | 2.0 | Cd | 2.0 | |
| I-14 | 360 | Cu | 40.0 | Cr | 2.0 | | | Acid clay added |
| I-15 | 360 | Cu | 40.0 | Cr | 2.0 | Cd | 2.0 | |

EXAMPLE 3

Reaction of silicon with 1:2 mixture of allyl chloride and hydrogen chloride 402 g of Si/Cu contact mixture (I-3) prepared in EXAMPLE 2 was charged in an agitating-type reaction bath, and dry nitrogen gas was blown into the reactor at the rate of 240 mi/min. After increasing the temperature in the reactor up to 300° C., allyl chloride was pumped using a syringe pump at the rate of 0.5 ml/min to the evaporator attached to the bottom of the reactor, while hydrogen chloride were also blown therein at the rate of 280 ml/min. 5 minutes after the initiation of pumping, increase of the temperature caused by an exothermic nature of the reaction was observed and reaction products began to flow along the wall of an receiver flask. While maintaining the above conditions, reaction product was taken every hour.

The obtained reaction products were analysed by using a gas chromatograph (packed column, SE-54, 0.9 m×⅛" OD.SS, TCD) and fractionally distilled to separate its constituents from one another, so that their structures could be determined. The structure of each constituent was determined by using a nuclear magnetic resonance spectroscopy and a mass spectrometry. After the reaction for 4 hours, 158.4 g of products was collected, while 112.7 g of allyl chloride was used.

The products contained 112.6 g (71.1%) of allyldichlorosilane (b.p 155°–157° C.; NMR (d, CDCl$_3$):5.85–5.71 (m, 1H, —CH=), 5.47 (t, 1H, Si—H), 5.18–5.12 (m, 2H, —CH$_2$—), 2.19–2.17 (d, 2H, —CH$_2$—)), and 6.5 g (4.1%) of allyltrichlorosilane (b.p. 115° C.; NMR (d, CDCl$_3$):5.87–5.73 (m, 1H,—CH=), 5.25–5.17 (m, 2H, CH$_2$50 ), 2.33–2.31 (d, 2H, —CH$_2$—). 24.8% of by-product contained 1.9 g (1.2%) of 1,1,4,4-tetrachloro-2-methyl-1,4-disilabutane (NMR (d, CDCl$_3$):5,66 (m, 1H, Si—H), 5.43 (s, 1H, Si—H), 1.69–1.61 (m, 1H, —CH=), 1.28 (d, 3H, CH$_3$—), 1.28–1.20 (m, 2H, —CH$_2$—)), 2.4 g (1.5%) of 1,1,5,5-tetrachloro-1,5-disilapentane (NMR (d, CDCl$_3$): 5.55 (t, 2H, Si—H), 1.89–1.78 (m, 2H, —CH$_2$), 1.38–1.32 (m, 4H, —CH$_2$—)), 4.8 g (3.0%) of 1,1,5,5-tetrachloro-3-dichlorosilyl-1,5-disilapentane (NMR (d, CDCl$_3$): 5.69 (t, 2H, Si—H), 5.60 (s, 1H, Si—H), 1.94 (d, 1H, —CH=), 1.68–1.45 (m, 4H, —CH$_2$—)) and the balance was 11.9% of trichlorosilane and 6.8% of tetrachlorosilane.

The reaction was carried out under the same condition and by the same reactor as employed above, except that the reaction temperature varied from 220° C. to 320° C. The results obtained from the reactions are shown in Table 2.

TABLE 2

| | Reaction Temperatures and Products composition | | | | | | | |
|---|---|---|---|---|---|---|---|---|
| Exp. No. | Reaction Temp (°C.) | Amt. of allyl chloride used (g) | Reaction time (hr) | Amt. of Products (g) | Composition of alkenyl silane (%) | | | Remark |
| | | | | | R'SiHCl$_2$ | R'SiCl$_3$ | Others | |
| 1 | 220 | 112.7 | 4.0 | 145.0 | 50.4 | 3.0 | 46.6 | |
| 2 | 240 | 112.7 | 4.0 | 146.4 | 52.3 | 3.7 | 44.0 | |
| 3 | 260 | 112.7 | 4.0 | 150.4 | 56.2 | 3.6 | 40.2 | |
| 4 | 280 | 112.7 | 4.0 | 156.0 | 61.9 | 3.7 | 34.4 | |
| 5 | 300 | 112.7 | 4.0 | 158.4 | 71.1 | 4.1 | 24.8 | |
| 6 | 320 | 112.7 | 4.0 | 151.5 | 58.8 | 4.7 | 36.5 | | wherein R' represents allyl group.

EXAMPLE 4

Reaction of silicon with mixtures of allyl chloride and hydrogen chloride

The reaction was carried out at 300° C. under the same condition and by the same reactor as employed in EXAMPLE 3, except that the mixing ratio of allyl chloride and hydrogen chloride varied from 1:1 to 1:3.

The results obtained from the reactions are shown in Table 3. The results shown in Exp. No. 9 of Table 3 are obtained from the reaction in which 20.0 g (5% based on the weight of the silicon and copper) of acid clay was added to the contact mixture. The contact mixture was recharged after 20% conversion and results were about same. Table 3: The reaction results obtained from various mixing ratio of reactants to products

TABLE 3

| | | | | The reaction results obtained from various mixing ratio of reactants to products | | | | | |
|---|---|---|---|---|---|---|---|---|---|
| No. | Amt. of Allyl chloride used (g) | Mixing Ratio | React. Time (hr) | Amt. of Products (g) | Composition of products (%) | | | Starting material | Remark |
| | | | | | R'SiHCl$_2$ | R'SiCl$_3$ | Others | | |
| 7 | 84.5 | 1:1.0 | 1.5 | 91.8 | 51.8 | 6.7 | 33.5 | 8.0 | |
| 8 | 84.5 | 1:1.5 | 1.75 | 102.6 | 61.0 | 5.3 | 33.7 | — | |
| 9 | 84.5 | 1:2.0 | 3.0 | 119.2 | 71.5 | 4.3 | 24.2 | — | Acid clay |
| 10 | 84.5 | 1:3.0 | 4.5 | 139.5 | 37.8 | 28.4 | 33.8 | — | | wherein R' represents allyl group

EXAMPLE 5

Reaction of contact mixtures with mixtures of allyl chloride and hydrogen chloride The reaction was carried out under the same condition and by the same reactor as employed in Exp. No. 5 of Example 3, except that the different contact mixture was used. All the contact mixture listed in Table 1 have been tested and the results obtained from the reactions are shown in Table 4.

TABLE 4

| | | | | Contact Mixtures and Product Compositions | | | | | |
|---|---|---|---|---|---|---|---|---|---|
| Exp. No. | Contact Mixture | Amt. of Allyl chloride used (g) | React. Time (hr) | Amt. of Products (g) | Composition of products (%) | | | Starting material | Remark |
| | | | | | R'SiHCl$_2$ | R'SiCl$_3$ | Others | | |
| 10 | I-1 | 112.7 | 1.5 | 81.9 | 40.3 | 15.4 | 45.0 | — | |
| 11 | I-2 | 84.5 | 3.0 | 99.5 | 46.0 | 17.2 | 36.8 | — | |

TABLE 4-continued

| | | | | Composition of products (%) | | | | |
|---|---|---|---|---|---|---|---|---|
| Exp. No. | Contact Mixture | Amt. of Allyl chloride used (g) | React. Time (hr) | Amt. of Products (g) | R'SiHCl$_2$ | R'SiCl$_3$ | Others | Starting material | Remark |
| 12 | I-4 | 112.7 | 4.0 | 134.6 | 31.0 | 14.9 | 54.1 | — | |
| 13 | I-5 | 112.7 | 4.0 | 135.7 | 25.7 | 41.7 | 22.9 | 9.7 | |
| 14 | I-6 | 84.5 | 3.0 | 127.6 | 10.3 | 25.3 | 64.4 | — | |
| 15 | I-7 | 84.5 | 3.0 | 125.3 | 18.4 | 23.7 | 57.9 | — | |
| 16 | I-8 | 84.5 | 3.0 | 132.9 | 19.5 | 53.2 | 27.3 | — | |
| 17 | I-9 | 84.5 | 3.0 | 120.7 | 45.7 | 21.3 | 33.0 | — | |
| 18 | I-10 | 84.5 | 3.0 | 115.3 | 20.2 | 44.5 | 35.3 | — | |
| 19 | I-11 | 84.5 | 3.0 | 121.2 | 48.5 | 25.4 | 26.1 | — | |
| 20 | I-12 | 84.5 | 3.0 | 119.4 | 18.5 | 50.3 | 30.8 | — | |
| 21 | I-13 | 84.5 | 3.0 | 123.5 | 39.1 | 25.2 | 35.7 | — | |
| 22 | I-14 | 84.5 | 3.0 | 121.5 | 13.2 | 45.6 | 41.2 | — | |
| 23 | I-15 | 84.5 | 3.0 | 124.7 | 51.4 | 15.2 | 33.4 | — | |
| 24 | I-16 | 84.5 | 3.0 | 117.4 | 23.8 | 43.7 | 32.5 | — | | wherein R' represents allyl group

EXAMPLE 6

Reaction of silicon with mixtures of allyl chloride and alkyl chloride lene, or ethylene respectively. When a half of the alkyl chloride was replaced by hydrogen chloride, the composition of the reaction products was about same as before. The results obtained from the reactions are shown in Table 5.

TABLE 5

Reaction Conditions and Product Compositions

| | | | | | Composition of products (%) | | | | |
|---|---|---|---|---|---|---|---|---|---|
| Exp. No. | Allyl chloride | Mixing Ratio | Amt. of Allyl chloride used (g) | React. Time (hr) | Amt. of Products (g) | R'SiHCl$_2$ | R'SiCl$_3$ | Others | Starting material | Remark |
| 25 | t-BuCl | 1:2 | 93.9 | 3.3 | 131.7 | 50.4 | 13.6 | 36.0 | — | |
| 26 | n-BuCl | 1:2 | 93.9 | 3.3 | 174.0 | 43.2 | 11.1 | 45.7 | — | |
| 27 | i-PrCl | 1:2 | 93.9 | 2.9 | 157.7 | 48.7 | 12.3 | 33.7 | 5.3 | |
| 28 | ClCH$_2$CH$_2$Cl | 1:1.2 | 93.9 | 2.4 | 163.9 | 21.9 | 55.7 | 22.4 | — | |

The following experiment demonstrates Exp. No. 25. The reaction was carried out at 300° C. under the same condition and by the same reactor as employed in Example 3, except that the same amount of t-butyl chloride was used as the hydrogen chloride source. 1:2 mixture of allyl chloride and t-butyl chloride was prepared by mixing 93.9 g (1.227 mole) of allyl chloride and 227.2 g (2.454 mole) of t-butyl chloride. The mixture was pumped at the rate of 100 ml/min to the evaporator attached to the bottom of the reactor, while N$_2$ was also blown therein at the rate of 280 ml/min. The gaseous by-product which was not trapped in the condenser was detected to be mostly isobutene produced from the decomposition of t-butyl chloride.

The reaction was carried out under the same condition and by the same reactor as employed above, except that the different mixing and different kind of alkyl chloride were used. n-Butyl chloride, i-propyl-chloride, or 1,2-dichloroethane was used instead of t-butyl chloride. In these cases, the gaseous by-product from the decomposition of alkyl chloride was 2-butene, propywherein R' represents allyl group.

EXAMPLE 7

Reaction of silicon with mixtures of allyl chloride and alkyl chloride in a fluidized bed reactor The reaction was carried out at 300° C. under the same condition as employed in Exp. 5 of Example 3, except that a fluidized bed reactor was employed instead of an agitating-type reaction bath. The reaction was also carried out under the same condition and by the same reactor as employed above, except that the alkyl chlorides used in Exp. 25, 26, 27 were used instead hydrogen chloride. The reaction conditions for Exp. 33 were same as those for Exp. 29 except that the pressure of the reactor was raised to 3 kg/cm$^2$. The results obtained from the reactions are shown in Table 6.

TABLE 6

Product Compositions of the Reaction using a Fluidized Bed Reactor

| | | | | | Composition of products (%) | | | | |
|---|---|---|---|---|---|---|---|---|---|
| Exp. No. | Allyl chloride | Amt. of Allyl chloride used (g) | React. Time (hr) | Amt. of Products (g) | R'SiHCl$_2$ | R'SiCl$_3$ | Others | Starting material | Remark |
| 29 | HCl | 112.7 | 4.0 | 126.5 | 14.5 | 27.4 | 27.8 | 30.3 | |
| 30 | n-BuCl | 93.9 | 3.3 | 127.8 | 12.5 | 30.7 | 24.2 | 32.6 | |
| 31 | t-BuCl | 93.9 | 3.3 | 97.8 | 16.7 | 34.3 | 13.4 | 35.6 | |
| 32 | i-PrCl | 93.9 | 2.9 | 95.2 | 14.7 | 28.5 | 17.3 | 39.5 | |
| 33 | HCl | 84.5 | 3.0 | 96.7 | 25.7 | 21.4 | 27.5 | 25.4 | 3.0 kg/cm$^2$ Reactor press | wherein R' represents allyl group

EXAMPLE 8

Reaction of silicon with a mixture of 1,3-dichloropropene and hydrogen chloride The reaction was carried out at 300° C. under the same condition and by the same reactor as employed in Example 3, except that 1,3-dichloropropene was used instead of allyl chloride and it's mixing ratio with hydrogen chloride was 1:3. After the reaction for 3 hours, 87.2 g of products was collected, while 70.9 g of 1,3-dichloropropene was used. The products contained 19.5 g (22.4%) of 1,1,5,5-tetrachloro-1,5-disilapenten (NMR (δ, CDCl$_3$):6.91–6.31 (m, 1H, —CH=), 6.10–5.90 (m, 1H, —CH=), 5.71–5.51 (m, 2H, Si—H), 2.60–2.40 (t, 2H, —CH$_2$—)) and 2.0 g (2.3%) of 3-chloro-2-propenyl-dichlorosilane. 75.3% of byproduct contained 30.6% of trichlorosilane and about 45% of the balance was unidentified substances.

EXAMPLE 9

Reaction of silicon with a mixture of 3-chloro-1-butene and hydrogen chloride The reaction was carded out under the same conditions and by the same reactor as employed in Example 8, except that 3-chloro-1-butene was used instead of 1,3-dichloropropene. After the reaction for 2 hours, 36.2 g of products was collected, while 36.0 g of 3-chloro-1-butene was used. The products contained 10.9 g (30.4%) of crotyldichlorosilane (NMR (δ, CDCl3):5.75–5.35 (m, 2H, —CH=), 5.44 (t, 1H, Si—H), 2.19–2.07 (m, 2H, —CH$_2$—), 1.72–1.64 (m, 3H, —CH$_3$)) and the ratio of cis- and trans-isomer was 1:1.5. The by-product contained 1.7 g (4.6%) of 1,1,6,6-tetrachloro-1,6-disila-3-hexene and 0.2 g (1.0%)of 1,1,1,6,6-pentachloro-1,6-disila-3-hexene. The rest of by-product contained 47.9% of trichlorosilane and about 16% of the balance was unidentified substances.

EXAMPLE 10

Reaction of silicon with a mixture of 3,4-dichloro-1-butene and hydrogen chloride The reaction was carried out at 280° C. under the same condition and by the same reactor as employed in Example 3, except that 3,4-dichloro-1-butene was used instead of allyl chloride and it's mixing ratio with hydrogen chloride was 1:1.5. After the reaction for 3 hours, 65.4 g of products was collected, while 69.0 g of 3,4-dichloro-1-butene was used. The products contained 17.5 g (26.8%) of 1,1,6,6-tetrachloro-1,6-disila-3-hexene (NMR, (δ, CDCl$_3$); 6.4–5.8 (m, 2H, —CH=), 5.9 (t, 2H, Si—H), 5.6–5.5 (m, 4H, —CH$_2$—)) and the ratio of cis- and trans-isomer was 1:1. The by-product contained 4.7 g (7.2%) of 1,1-dichloro-1-sila-3-cyclopentene, (NMR, (δ, CDCl$_3$); 5.99 (s, 2H, —CH=), 1.86(s, 2H, —CH$_2$—)), and 1.9 g (2.9%) of 1,1,1,6,6-pentachloro-1,6-disila-3-hexene. The rest of by-product contained 15.1 g (23.1%) of hexachlorodisilane and 11.5% of trichlorosilane.

What is claimed is:

1. Alkenylchlorosilanes of formula (I)

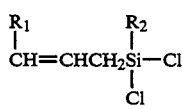  Formula (I)

wherein R$_1$ is SiHCl$_2$, SiCl$_3$ or CH$_2$SiCl$_3$ and R$_2$ is hydrogen.

2. A method for preparing alkenylchlorosilanes of formula (I) by direct reaction of silicon with a mixture of alkenylchloride of formula (II) incorporated and alkylchlorides of formula (III), in the presence of a copper catalyst at a temperature from 250° C. to 350° C.; wherein,

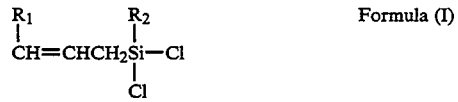  Formula (I)

in formula (I), R$_1$, represents SiHCl$_2$, SiCl$_3$ or CH$_2$SiCl$_3$ and R$_2$ represents hydrogen;

  Formula (II)

in formula (II), R$_3$ represents hydrogen or chlorine and R$_4$ represents hydrogen, methyl, or CH$_2$Cl; and $$Cl—R_5 \quad (III)$$

in formula (III), R$_5$ represnts hydrogen, C$_3$–C$_4$ alkyl or CH$_2$CH$_2$Cl.

3. The method in accordance with claim 1, wherein R$_3$ and R$_4$ are all hydrogen In formula (II).

4. The method in accordance with claim 2, wherein R$_3$ is hydrogen and R$_4$ is methyl group in formula (II).

5. The method in accordance with claim 2, wherein R$_3$ is hydrogen and R$_4$ is chloromethyl group in formula (II).

6. The method in accordance with claim 2, wherein R$_3$ is chloro group and R$_4$ is hydrogen in formula (II).

7. The method in accordance with claim 2, wherein R$_5$—Cl in formula (III) is hydrogen chloride.

8. The method in accordance with claim 2, wherein R$_5$ is propyl group in formula (III).

9. The method in accordance with claim 2, wherein R$_5$ is n-butyl group in formula (III).

10. The method in accordance with claim 2, wherein R$_5$ is t-butyl group in formula (III).

11. The method in accordance with claim 2, wherein R$_5$ is chloroethyl group in formula (III).

12. The method in accordance with claim 2, wherein 0.5–4 times of alkyl chloride in formula (III) is added to each mole of alkenyl chloride in formula (II).

13. The method in accordance with claim 12, wherein R$_5$—Cl in formula (III) Is 1:1 mixture of butyl chloride and hydrogen chloride.

14. The method in accordance with claim 2, wherein a stirred bed reactor equipped with a spiral band agitator or fluidized bed reactor is used.

15. The method in accordance with claim 2, wherein the pressure of reactor is 1–5 atmospheric pressure.

16. The method in accordance with claim 2, wherein in the reaction about 1–50 wt % of micro-spherical acid clay based on the amount of silicon is added, 17. The method in accordance with claim 2, wherein about 1–20 wt. % of copper or cuprous chloride based on the amount of silicon is added.

18. The method in accordance with claim 2, wherein about 0.01–5 wt. % of calcium, barium, zinc, tin, cadmium, manganese, magnesium, silver, chromium, based on the amount of silicon is added as the co-catalyst.

19. The method in accordance with claim 2, wherein the reaction is run continuously by feeding the contact mixtures as they are consumed.

* * * * *